US011415003B2

(12) United States Patent
Loisel et al.

(10) Patent No.: US 11,415,003 B2
(45) Date of Patent: Aug. 16, 2022

(54) METHOD FOR PRODUCING A METAL BLADED ELEMENT OF AN AIRCRAFT TURBINE ENGINE

(71) Applicant: SAFRAN AIRCRAFT ENGINES, Paris (FR)

(72) Inventors: Bruno Marc-Etienne Loisel, Cormeilles-en-Parisis (FR); Guillaume Sylvain Frédéric Evrard, Trappes (FR); Alexandre Thanh Nhan Nguyen, Paris (FR); Carine Thuy-Huong Pragassam, Courbevoie (FR)

(73) Assignee: SAFRAN AIRCRAFT ENGINES, Paris (FR)

( * ) Notice: Subject to any disclaimer, the term of this patent is extended or adjusted under 35 U.S.C. 154(b) by 0 days.

(21) Appl. No.: 16/377,708

(22) Filed: Apr. 8, 2019

(65) Prior Publication Data
US 2019/0309638 A1 Oct. 10, 2019

(30) Foreign Application Priority Data

Apr. 10, 2018 (FR) ........................................ 1853135

(51) Int. Cl.
*F01D 5/28* (2006.01)
*G01N 33/208* (2019.01)
(Continued)

(52) U.S. Cl.
CPC .............. *F01D 5/288* (2013.01); *B23K 35/00* (2013.01); *F01D 5/00* (2013.01); *G01B 3/30* (2013.01);
(Continued)

(58) Field of Classification Search
CPC . F01D 5/288; F01D 5/22; F01D 5/225; F01D 5/00; F01D 5/005; F01D 21/003;
(Continued)

(56) References Cited

U.S. PATENT DOCUMENTS 989,512 A * 4/1911 Honegger ................ G01B 3/30
33/562
2,607,125 A * 8/1952 Johansson ................ G01B 3/30
33/567

(Continued)

FOREIGN PATENT DOCUMENTS

FR 2512542 A1 3/1983
FR 2640285 A1 6/1990
(Continued)

OTHER PUBLICATIONS

Welder's Visual Inspection Handbook, May 2013 (Year: 2013).*
(Continued)

*Primary Examiner* — David E Sosnowski
*Assistant Examiner* — Wayne A Lambert
(74) *Attorney, Agent, or Firm* — Christensen O'Connor Johnson Kindness PLLC

(57) ABSTRACT

A method for producing a metal bladed element of a turbine engine, in particular of an aircraft, includes steps of producing the bladed element, depositing a coating made of wear-proof material on at least one portion of the bladed element and verifying, preferably visually, the conformity of the bladed element. Verifying the conformity of the bladed element includes implementing a verification element on the bladed element. The bladed element is configured according to a conformity threshold value to conceal a non-conformity of the coating, if the non-conformity has at least one dimension less than the threshold value, and to show at least one portion of this non-conformity if the at least one dimension is greater than the threshold value.

12 Claims, 3 Drawing Sheets

(51) Int. Cl.
  *F01D 5/00* (2006.01)
  *G01B 3/30* (2006.01)
  *B23K 35/00* (2006.01)

(52) U.S. Cl.
  CPC ....... *G01N 33/208* (2019.01); *F05D 2230/90* (2013.01); *F05D 2260/83* (2013.01); *F05D 2300/611* (2013.01)

(58) Field of Classification Search
  CPC ............. F05D 2260/80; F05D 2260/83; F05D 2230/90; F05D 2230/31; F05D 2250/20; F05D 2300/611; G01B 21/16; G01B 3/30; G01N 33/208; B23K 35/00
  See application file for complete search history.

(56) References Cited

U.S. PATENT DOCUMENTS

| | | | | |
|---|---|---|---|---|
| 4,090,302 A * | 5/1978 | Bollmer | ................... | G01B 3/30 33/567 |
| 4,155,152 A * | 5/1979 | Cretella | ................. | B23P 6/007 29/889.1 |
| 4,257,741 A * | 3/1981 | Betts | ....................... | B22F 7/064 228/122.1 |
| 4,291,448 A * | 9/1981 | Cretella | ................. | B23P 6/007 29/402.07 |
| 4,957,567 A | 9/1990 | Krueger et al. | | |
| 5,890,274 A * | 4/1999 | Clement | ................ | B23P 6/005 29/527.2 |
| 6,164,916 A * | 12/2000 | Frost | ................. | B23K 35/3046 148/528 |
| 6,701,616 B2 * | 3/2004 | Smith | .................... | B23P 6/007 29/402.09 |
| 7,001,152 B2 * | 2/2006 | Paquet | .................... | F01D 5/225 29/889.21 |
| 7,509,736 B2 * | 3/2009 | Boudereau | .............. | B23P 6/007 29/889.1 |
| 7,771,171 B2 * | 8/2010 | Mohr | ...................... | F01D 5/225 416/191 |
| 7,934,315 B2 * | 5/2011 | Milleville | ............... | F01D 5/005 29/889.1 |
| 2004/0124231 A1 * | 7/2004 | Hasz | .................... | B23K 35/327 228/245 |
| 2008/0229598 A1 * | 9/2008 | Liu | ......................... | G01B 3/20 33/562 |
| 2013/0259699 A1 | 10/2013 | Collin et al. | | |
| 2015/0023793 A1 | 1/2015 | Bensalah et al. | | |
| 2015/0369058 A1 | 12/2015 | Negri et al. | | |
| 2019/0041191 A1 | 2/2019 | Arquie | | |

FOREIGN PATENT DOCUMENTS

| | | | | |
|---|---|---|---|---|
| FR | 2967714 A1 * | 5/2012 | ............. | F01D 5/225 |
| FR | 2967714 A1 | 5/2012 | | |
| FR | 2985759 A1 | 7/2013 | | |
| FR | 3047310 A1 | 8/2017 | | |
| GB | 2121177 A | 12/1983 | | |
| WO | 2014/118456 A1 | 8/2014 | | |

OTHER PUBLICATIONS

Primo, Welding Inspection Qualifications & testing Procedures, 2012 (Year: 2012).*

Rapport de Recherche Préliminaire dated Jan. 16, 2019, issued in corresponding French Application No. 1853135 filed Apr. 10, 2018, 7 pages.

* cited by examiner

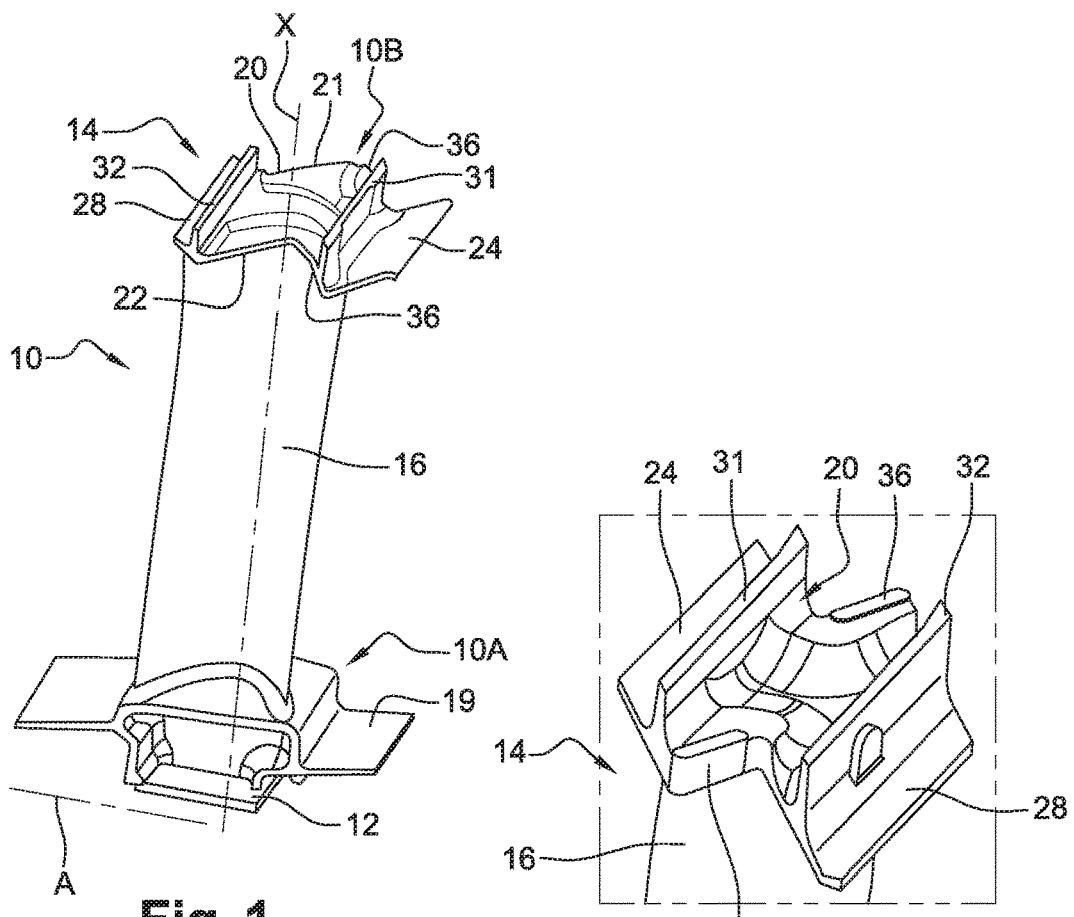
Fig. 1 (PRIOR ART)
Fig. 2
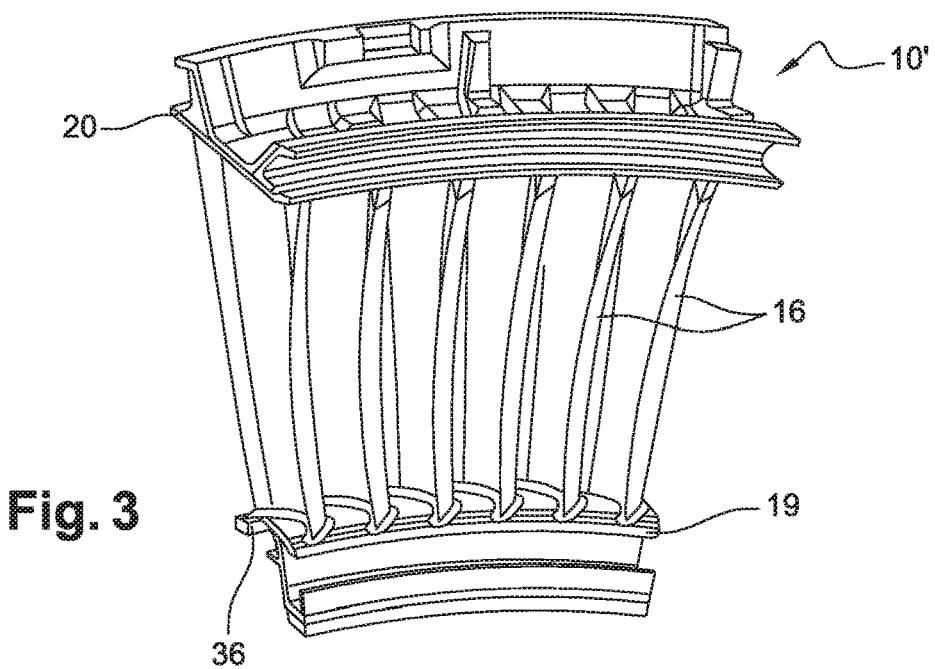
Fig. 3

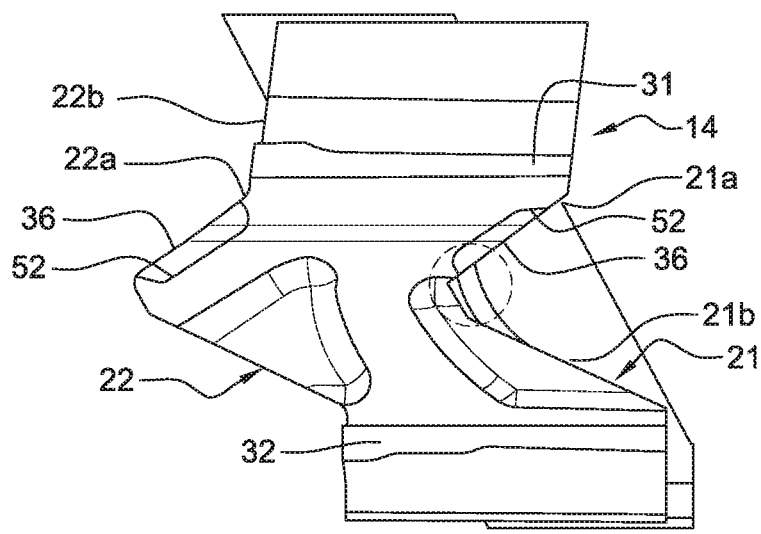
Fig. 4
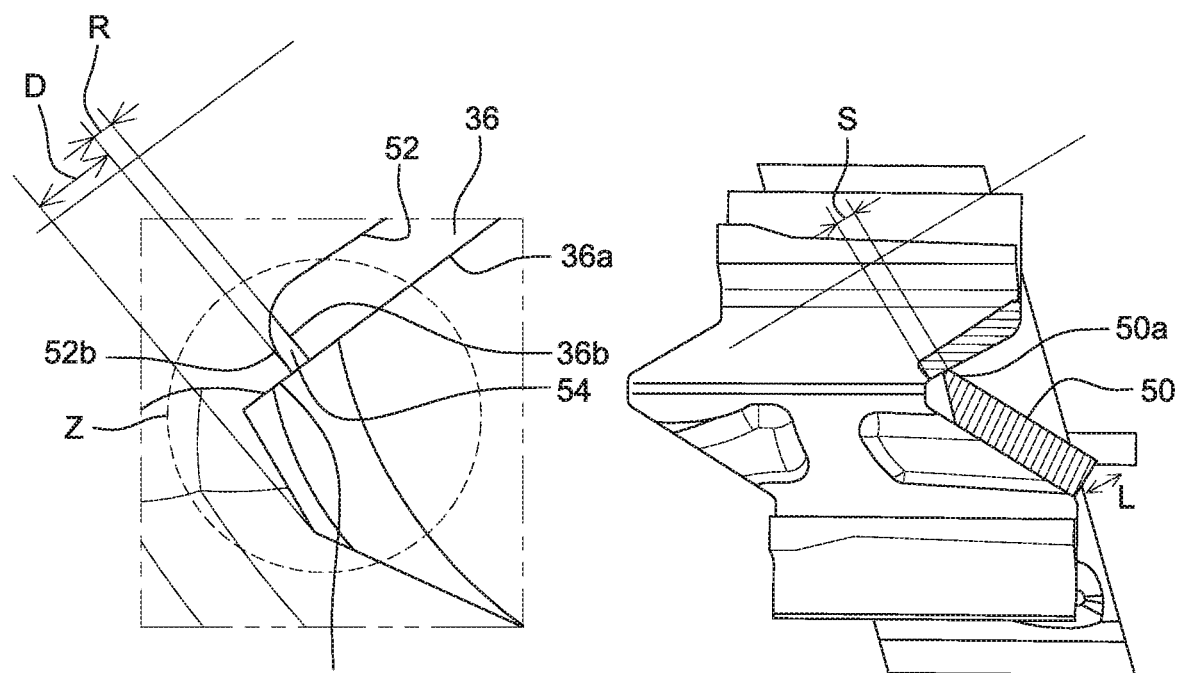
Fig. 4a
Fig. 5
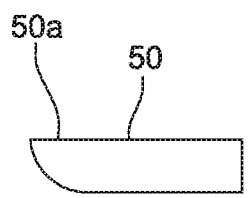
Fig. 6a
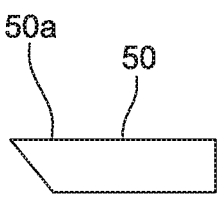
Fig. 6b
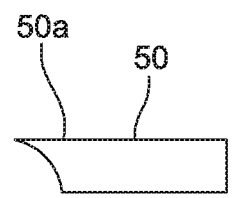
Fig. 6c

METHOD FOR PRODUCING A METAL BLADED ELEMENT OF AN AIRCRAFT TURBINE ENGINE

BACKGROUND

The state of the art comprises documents FR 3 047 310 A1, FR 2 512 542 A1, FR 2 640 285 A1, FR 2 985 759 A1, WO 2014/118456 A1 and FR 2 967 714 A1.

The axial turbine of the turbine engine is composed of a succession of axial stages (along the gas stream circulation axis) arranged behind one another. Each stage comprises a mobile wheel with blades forming the rotor and a bladed nozzle forming the stator. The mobile wheel is rotated opposite the corresponding nozzle.

In the present disclosure, the upstream and downstream are defined with respect to the normal flow direction of the air streams (from upstream to downstream) through the turbine engine. The "axis of the turbine engine" is called the rotation axis of the main rotor of the turbine engine. The axial direction corresponds to the direction of the axis of the turbine engine, and a radial direction is a direction perpendicular to the axis of the turbine engine and cutting this axis. Likewise, an axial plane is a plane containing the axis of the turbine engine, and a radial plane is a plane perpendicular to this axis. The adjectives "inner" and "outer" are used in reference to a radial direction, such that the inner portion of an element is, along a radial direction, closer to the axis of the turbine engine than the outer portion of the same element. The stacking axis of a blade is the axis perpendicular to the axis of the turbine engine, which passes through the centre of gravity of the section that is most inside the vane of the blade (i.e. the section closest to the axis of the turbine engine). In some embodiments, the turbine engine blade comprises a vane extending along the stacking axis of the blade, between the proximal and distal ends (i.e. inside and outside) of the blade.

The mobile wheel is conventionally constituted of an annular disc centered on the rotation axis of the wheel, on which are secured a plurality of blades.

An example blade is represented in FIG. 1. A blade of this type is described in patent document FR-B1-2 985 759. This blade 10 comprises a vane 16 extending along the stacking axis X of the blade, between the proximal 10A and distal 10B ends of the blade 10. At the proximal end 10A thereof, the blade 10 comprises a platform 19 and a base 12 by which it is secured to the disc (not represented). At the distal end 10B, the blade 10 has a heel 14. When several blades 10 are secured on the disc, the heels 14 are arranged edge-to-edge so as to form a circumferential crown delimiting a revolution surface about the rotation axis A of the wheel. This crown in particular delimits the outer surface of the flow passage of the gas streams circulating between the vanes 16 and of limiting gas leaks at the level of the distal end 10B of the blades 10.

The heel 14 comprises a platform 20 externally delimiting the flow passage of the gas circulating between the vanes 16, and having opposite side edges 21, 22. The platform 20 comprises an upstream portion 24 called "upstream spoiler" and a downstream portion 28 called "downstream spoiler." The heel 14 also comprises upstream 31 and downstream 32 rubbing strip seals extending radially towards the outside from the outer face of the platform 20. Each of the side edges 21, 22 of the platform has, between the upstream 31 and downstream 32 rubbing strips, a substantially U-shaped profile. In the case of other blades, this profile can take the shape of a "Z" or of a "V," for example.

With the aim of damping the vibrations to which the blades 10 are subjected when functioning, and to give rigidity to the assembly, the blades 10 are mounted on the disc thereof with a torsional stress about a torsion axis positioned with respect to the stacking axis X. The geometry of the heels 14 is such that each blade 10 is torsion-stressed by bearing on the adjacent blades 10 at the level of the side edges 21 and 22. These side edges 21, 22 therefore define the inter-blade contact surfaces and are the place of significant frictions during the functioning of the turbine engine. To be protected against wear, these edges are provided with a coating made of a friction-resistant, wear-proof material. It can, for example, relate to a material commercialised under the brand STELLITE®. This coating 36 can be seen in FIG. 2.

Conventionally, this wear-proof coating 36 is deposited on the side edges 21, 22 by welding, for example by tack welding, involving the creation of an electric arc for melting the material. Applying the coating 36 may be a manual operation, the STELLITE®-type alloy being in the form of a liquid drop during deposition.

The STELLITE® alloy is a steel alloy with high chromium (Cr) and cobalt (Co) content. It can also contain a small quantity of tungsten (W) or molybdenum (Mo) and a small quantity of carbon (C). The STELLITE® alloy cannot be forged and must be molded, that is secured by welding on an object, of which it forms a portion or to which it is inserted.

Parts used in the aeronautic industry must generally conform with a specific set of specifications. Levels of conformity of these parts are established by determining a threshold and by verifying if the part does or does not reach the established threshold. If the part reaches the established thresholds, the part is labelled level 1 (C1) conformity. If the part does not reach the established thresholds, the part would be labelled level 2 (C2) conformity.

A bladed element with a wear-proof material coating must be verified to validate the conformity thereof, and in particular verify the presence of potential non-conformities of the coating, which must be as small as possible.

The present disclosure proposes a simple, effective, and economic solution to this problem.

SUMMARY

Various embodiments of the present disclosure provide a method for producing a metal bladed element of a turbine engine, in particular an aircraft turbine engine. The method includes producing the bladed element, depositing a coating made of wear-proof material on at least one portion of the bladed element, and verifying, sometimes visually, the conformity of the bladed element. Verifying includes implementing a verification element on the bladed element, this element being configured according to a conformity threshold to conceal a non-conformity of the coating, if this non-conformity has at least one dimension less than this threshold value, and to leave visible at least one portion of this non-conformity if the at least one dimension is greater than this threshold value.

The verification of the conformity of the bladed element here comes back to verifying the conformity (of the deposition) of the coating made of deposited wear-proof material. This coating can have a non-conformity such as, for example, an incorrect spread of the wear-proof material, which leads to a breach. In the present disclosure, a conformity criterion of this non-conformity is predetermined and here is a dimensional criterion. At least one dimension of this non-conformity must be less than a predetermined threshold value. If this dimension is less than the threshold (and, in some embodiments, zero in the absence of non-conformity), the bladed element could be considered as having a conformity level C1. In the alternative embodiments, where this dimension would be greater than the threshold, the bladed element may be labelled a conformity level C2. In some embodiments, the method according to the present disclosure uses at least one verification element which is placed on the bladed element and makes it possible to conceal or show the possible non-conformity of the bladed element. When the dimension of the defect would be less than the threshold, the non-conformity would be concealed by the verification element positioned on the bladed element. Alternately, when this dimension would be greater than the threshold, the non-conformity would at least partially be shown, as the verification element could not totally conceal it, even not at all.

In another embodiment, after the depositing step, the method may include machining the bladed element and the coating. Additionally or alternatively, the method may then include penetrant testing the bladed element. The bladed element may include side edges which cooperate by interlocking with side edges of other identical bladed elements, these side edges having at least partially one V- or L-shaped hollow shape comprising two edge portions. In some embodiments, one first edge portion may include the coating wherein the coating is applied in the depositing step in a cavity of the first edge portion. The at least one dimension may be measured in a direction substantially parallel to said first edge portion comprising the coating or perpendicular to a second edge portion. In some embodiments, the verification element is supported against the second edge portion in the depositing step and comprises an end intended to bear against an end of the coating in order to conceal a non-conformity of this end of which at least one dimension would be less than the conformity threshold value. In alternative embodiments, the dimension is a maximum distance measured between the end of the coating and an end closest to the cavity. In some instances, the verification element has an extended shape and is shaped to bear against and extend longitudinally over substantially the whole length of the second edge portion. In still further embodiments, the end of the verification element is tapered.

The present disclosure also relates to an assembly comprising a bladed element of a turbine engine and an element for verifying the conformity of this bladed element, for the implementation of the method such as described above. The bladed element can be a turbine engine rotor blade or a nozzle.

DESCRIPTION OF THE DRAWINGS

The foregoing aspects and many of the attendant advantages of the claimed subject matter will become more readily appreciated as the same become better understood by reference to the following detailed description, when taken in conjunction with the accompanying drawings, wherein:

FIG. 1 is a schematic, perspective view of a known turbine mobile wheel blade;

FIG. 2 is a schematic view on a larger scale of an exemplary heel of a turbine mobile wheel blade;

FIG. 3 is a schematic view of an exemplary turbine nozzle sector;

FIG. 4 is a schematic view on a larger scale of another exemplary heel of a turbine mobile wheel blade;

FIG. 4a is an even larger scale view of the exemplary heel of FIG. 4;

FIG. 5 is a schematic view of an exemplary heel similar to that of FIG. 4 and illustrates an exemplary step of the method according to the present disclosure;

FIGS. 6a, 6b, and 6c are schematic views of exemplary verification elements according to the present disclosure;

DETAILED DESCRIPTION

Figure 7:
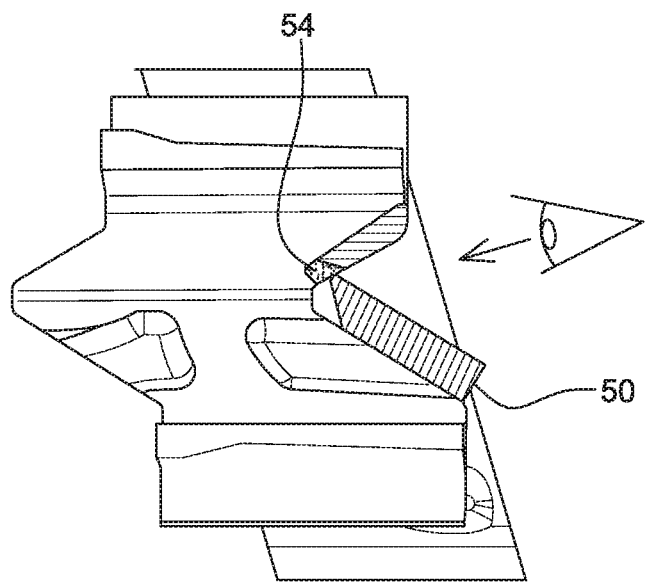
FIG. 7, FIG. 7a, FIG. 8, and FIG. 8a are schematic views of an exemplary heel similar to FIG. 5, where the figures illustrate an exemplary step of the method according to the present disclosure.

The detailed description set forth below in connection with the appended drawings, where like numerals reference like elements, is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

Various embodiments of the present disclosure relate to the general field of producing metal bladed elements for an aircraft turbine engine, the bladed elements comprising stator or rotor elements.

The present disclosure applies to a bladed element which can be a mobile wheel blade 10 such as described above in reference to FIGS. 1 and 2, or a turbine nozzle 10' as illustrated in FIG. 3.

In either embodiment, the bladed element comprises at least one vane 16 which extends between two platforms, respectively inner 19 and outer 20. The inner platform 19 is connected to the radially inner end of each vane and comprises coatings 36 made of wear-proof material in the case of the turbine nozzle sector of FIG. 3. The outer platform 20 is connected to the radially outer end of each vane and comprises coatings 36 made of hard wear-proof material in the case of the blade of FIGS. 1 and 2.

Figure 9:
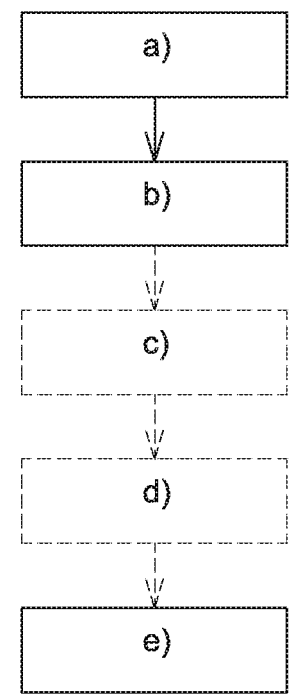
FIG. 9 is a block diagram illustrating exemplary steps of a method for producing a blade element, according to the present disclosure.

FIG. 9 illustrates an exemplary method according to the method for producing a bladed element. In some embodiments, at block a, the method includes producing the bladed element, at block b, depositing the coating 36 made of wear-proof material on at least one portion of the bladed element, and, at block e, verifying the conformity of the bladed element. In some embodiments, producing the bladed element may include casting the element. In some instances, depositing the wear-proof material may include a tack welding or an alternative welding technique, as stated above.

In alternative embodiments, after block b, the method, at block c, may include machining the bladed element and the coating 36. Machining the bladed element and the coating may put the bladed element at predefined sides and improve the surface state of the coating. After block c, the method may additionally or alternatively, at block d, include penetrant testing the bladed element. The penetrant testing may be performed on the bladed element to facilitate the detection of non-conformities in the verification step.

In some embodiments, at block e, an operator performs the verification of the bladed element using at least one verification element 50, such as a wedge or a cover, which is positioned on the bladed element. The operator may visually verify the conformity of the bladed element using this verification element 50.

As shown in FIGS. 6a-6c, the verification element 50 may conceal a non-conformity of the coating 36 when the non-conformity has at least one dimension less than a conformity threshold value, and to show at least one portion of this non-conformity if the dimension of this non-conformity is greater than the threshold value.

FIG. 4 shows an exemplary mobile blade heel 14 with coatings 36. The heel 14 comprises an outer platform 20 having opposite side edges 21, 22. The heel 14 also comprises upstream 31 and downstream 32 rubbing strip seals extending radially towards the outside from the outer face of the platform 20. Each of the side edges 21, 22 of the platform has, between the upstream 31 and downstream 32 rubbing strips, a substantially Z-shaped or V-shaped profile, which comprises two edge portions defining between them a cavity and of which one is coated with wear-proof material.

In some embodiments, the side edge 21 thus comprises two edge portions 21a, 21b which form a V-shaped dihedron or a cavity, the wear-proof coating 36 being situated on the edge portion 21a. The side edge 22 comprises two edge portions 22a, 22b which form a V-shaped dihedron or a cavity, the wear-proof coating 36 being situated on the edge portion 22a.

In some instances, each edge portion 21a, 22a that receives the wear-proof coating 36 comprises a cavity 52 which is filled with wear-proof material. As can be seen in the drawings, the cavity 52 is fully filled with material. The coating 36 can be deposited in the cavity 52 then the machining provided in at block d can be designed to flatten the visible surface 36a of the coating, and ensure this surface is aligned with adjacent surfaces 52a of the edge portion 21a, 22a.

FIG. 4a is a larger scale view of a portion of FIG. 4 and more specifically of one of the ends of the cavity 52 and of the coating, as well as the zone for connecting the abovementioned two edge portions 21a, 21b, here for the hollow dihedron of the side edge 21.

In some instances, a non-conformity 54, such as a lack of coating, may be present in the zone Z for joining the end 36a of the wear-proof material to the end 52b closest to the cavity. When this non-conformity 54 is small in size, the non-conformity 54 is not necessarily visible and may be considered acceptable. The bladed element could therefore be considered as conforming with level C1 following the verification step at block e. When this non-conformity is too large in size, the non-conformity is visible. The bladed element could therefore be considered as conforming with level C2 following the verification step at block e.

In the examples shown, a non-conformity dimension is considered, namely a dimension measured in a direction substantially parallel to the edge portion 21a, 22a on which is deposited the coating. The dimension is, for example, the offset dimension or lack of wear-proof material in the cavity 52, which would be measured between the abovementioned two ends 36a, 52b and which is schematically represented by the letter R in FIG. 4a.

When dimension R is less than a predetermined threshold value, referenced S, FIG. 5, the bladed element can be considered as conforming with level C1, and when dimension R is greater than S, the bladed element can be considered as conforming with level C2.

This comparison is made visually by means of the verification element 50, as is represented in FIG. 5. For example, at block e in FIG. 9, the method may include implementing the verification element 50 on the bladed element to verify if the potential non-conformity is of level C1 or C2. In the example shown, the verification element 50 is positioned on the edge portion 21b or 22b which does not comprise any coating. The verification element 50 has an extended shape and is shaped to bear against and extend longitudinally over the whole length of this edge portion 21b, 22b.

The verification element 50 comprises a longitudinal end intended to bear against the end 36a of the coating 36 in order to conceal the potential non-conformity 54 of this end. The verification element 50 is furthermore shaped and in particular sized such that it conceals the non-conformity if the dimension R thereof is less than S, and to show at least one portion of this non-conformity if dimension R is greater than S.

In some embodiments, the end 50a of the verification element 50 is tapered to improve the precision of the verification, which may be visually performed by an operator. This end 50a can have any truncated shape and, examples of which are shown in in FIG. 6a (with a lower convex edge, this lower edge being oriented towards the edge portion 21b, 22b on which the verification element bears against it), FIG. 6b (tapered or truncated), and FIG. 6c (with a lower concave edge).

In some embodiments, the dimension L (see FIG. 5) of the verification element 50 measured in the abovementioned direction is determined according to the threshold value S (from the time when the edge portions are substantially perpendicular). If D is considered, as being the dimension of the non-conformity, measured in the abovementioned direction, between the edge portion 21b, 22b and the end 52a of the cavity, thus $L=S+D$.

In some embodiments, a truncated edge, as stated above, may ensure a correct positioning of the verification element 50. For example, disruptive element is lacking here as the verification element 50 comes to bear against a predefined surface and the distance L making it possible to taper in the desired zone.

Figure 7A:
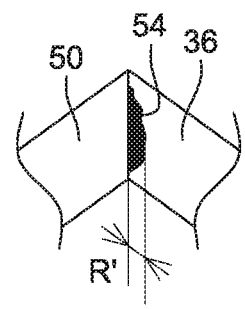

FIG. 7 shows an example where the bladed element would be classified as conformity level C2 as the non-conformity has a dimension greater than S. The operator watching the zone Z could thus assess an image such as schematically represented in FIG. 7a. The non-conformity would be too significant, the dimension R thereof being greater than the threshold S. In other words, L would be less than D+R, which would make a portion of the non-conformity visible, namely a portion having as a dimension $R'=(R+D-L)$.

Figure 8:
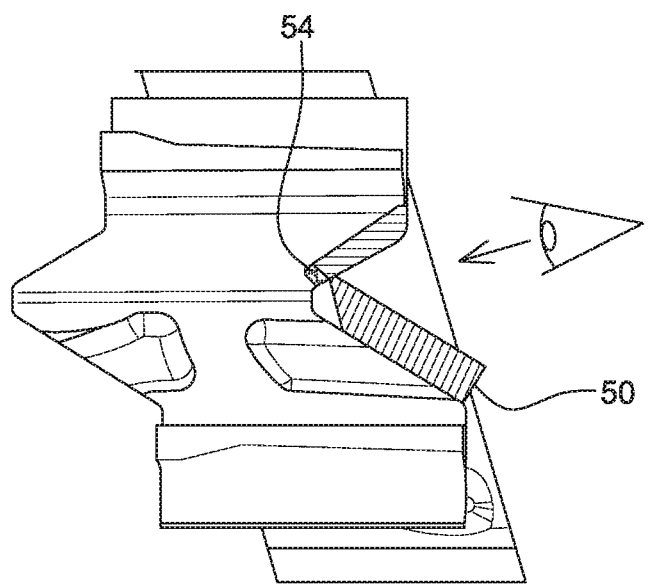
Figure 8A:
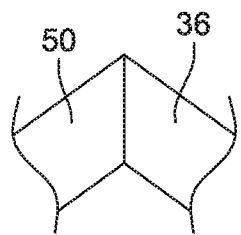

FIG. 8 shows an example where the bladed element would be classified as conformity level C1, as the non-conformity has a dimension less than S. The operator watching the zone Z could thus assess an image such as schematically represented in FIG. 8a. The non-conformity would be concealed by the verification element, the dimension R thereof being less than the threshold S. In other words, L would be greater than D+R, which would make the non-conformity invisible.

In an alternative embodiment, the dimension of the non-conformity could be measured in a direction perpendicular to the edge portion 21b, 22b on which is positioned the verification element 50, such that L corresponds to the thickness of the verification element measured from this edge portion.

In some embodiments, the present disclosure can be applied to a turbine nozzle 10' such as represented in FIG. 3, as this nozzle also includes two edge portions forming a hollow L, of which one is covered with a wear-proof material and the other can receive a verification element.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

The embodiments of the invention in which an exclusive property or privilege is claimed are defined as follows:

1. A method for producing a metal bladed element of a turbine engine, the method comprising:
   producing the bladed element;
   depositing a coating comprising a wear-proof material on at least one portion of the bladed element; and
   verifying, visually, conformity of the coating by implementing a verification element on the bladed element, wherein:
   a non-conformity of the coating is concealed by a thickness of the verification element when the non-conformity has at least one dimension less than a threshold value, or
   at least one portion of the non-conformity is exposed when the at least one dimension is greater than the threshold value,
   wherein the bladed element comprises side edges configured to interlock with side edges of other identical bladed elements, these side edges having at least partially one of a V-shaped and L-shaped hollow-shape comprising first and second edge portions of which the first edge portion comprises the coating,
   wherein the verification element is supported against the second edge portion in the verifying step and comprises an end configured to bear against an end of the coating to either conceal the non-conformity when the non-conformity has at least one dimension less than the threshold value or to expose the non-conformity when the non-conformity has at least one dimension greater than the threshold value, and
   wherein the end of the verification element is tapered.

2. The method according to claim 1, further comprising machining the bladed element and the coating after the coating is deposited on the bladed element.

3. The method according to claim 1, wherein the coating is deposited in a cavity of the first edge portion.

4. The method according to claim 1, wherein the at least one dimension is a maximum distance measured between the end of the coating and an end closest to the cavity.

5. The method according to claim 1, wherein the verification element has an extended shape and is shaped to bear against and extend longitudinally over the whole length of the second edge portion.

6. An assembly comprising a bladed element of a turbine engine and a verification element, for implementing the method according to claim 1.

7. The assembly according to claim 6, wherein the bladed element is one of a turbine engine rotor blade or a turbine engine nozzle.

8. The method according to claim 2, further comprising penetrant testing the bladed element.

9. The method according to claim 1, further comprising penetrant testing the bladed element after the coating is deposited on the bladed element.

10. The method according to claim 1, wherein the turbine engine is of an aircraft.

11. The method according to claim 1, wherein the end of the verification element comprises a lower concave edge.

12. The method according to claim 1, wherein the end of the verification element comprises a lower convex edge, the lower edge being oriented towards the side edges.

* * * * *